(12) United States Patent
Shah et al.

(10) Patent No.: US 8,167,859 B2
(45) Date of Patent: May 1, 2012

(54) OSTOMY BAG MOUNTING STRUCTURE

(75) Inventors: Tilak M. Shah, Cary, NC (US); Dylan Hege, Cary, NC (US); Jessica K. Crews, Raleigh, NC (US)

(73) Assignee: Polyzen Inc., Apex, NC (US)

( * ) Notice: Subject to any disclaimer, the term of this patent is extended or adjusted under 35 U.S.C. 154(b) by 414 days.

(21) Appl. No.: 12/106,743

(22) Filed: Apr. 21, 2008

(65) Prior Publication Data

US 2008/0262449 A1    Oct. 23, 2008

Related U.S. Application Data

(60) Provisional application No. 60/913,529, filed on Apr. 23, 2007.

(51) Int. Cl.
*A61F 5/44* (2006.01)

(52) U.S. Cl. ...... 604/339; 604/327; 604/328; 604/332; 604/338; 604/343; 604/352; 604/382; 604/103.03

(58) Field of Classification Search ............ 604/339, 604/352, 382, 103.3, 343, 327, 328, 332, 604/338, 103.03
See application file for complete search history.

(56) References Cited

U.S. PATENT DOCUMENTS

| | | | |
|---|---|---|---|
| 3,447,533 A * | 6/1969 | Spicer | 600/32 |
| 3,848,602 A | 11/1974 | Gutnick | |
| 3,915,171 A | 10/1975 | Shermeta | |
| 4,022,216 A * | 5/1977 | Stevens | 604/101.03 |
| 4,043,345 A | 8/1977 | Kramann et al. | |
| 4,311,146 A | 1/1982 | Wonder | |
| 4,327,736 A * | 5/1982 | Inoue | 604/101.05 |
| 4,464,175 A | 8/1984 | Altman et al. | |
| 4,555,242 A * | 11/1985 | Saudagar | 604/103.08 |
| 4,650,463 A | 3/1987 | LeVeen et al. | |
| 4,662,890 A * | 5/1987 | Burton | 623/1.31 |
| 4,664,114 A * | 5/1987 | Ghodsian | 606/193 |
| 4,685,901 A | 8/1987 | Parks | |

(Continued)

FOREIGN PATENT DOCUMENTS

JP    51-090376 A    8/1976

(Continued)

OTHER PUBLICATIONS

Co-pending U.S. Appl. No. 12/106,760, entitled, "Extrusion Blow-Molded Corporeal Port Mounting Structure" filed Apr. 21, 2008 in the name of Tilak Shah.

*Primary Examiner* — Tatyana Zalukaeva
*Assistant Examiner* — Ginger T Chapman
(74) *Attorney, Agent, or Firm* — Hultquist, PLLC; Steven J. Hultquist

(57) ABSTRACT

A mounting structure for installation at a corporeal port opening. The mounting structure includes a reentrant tube on an exterior surface of which is disposed at least one balloon, with a proximal everted portion of the tubing extending from the distal portion of the tubing, with a gas flow passage associated with the tubing, for selective inflation of the balloon. A vacuum thermoforming process for making such mounting structure is described. The mounting structure is useful employed for anchoring of a therapeutic device such as an ostomy bag at a corresponding port of the body, with the balloon(s) of the device providing effective anchoring of the mounting structure and permitting the mounting structure to be comfortably worn by a patient during therapeutic intervention.

31 Claims, 8 Drawing Sheets

U.S. PATENT DOCUMENTS

| | | | |
|---|---|---|---|
| 4,693,236 A | | 9/1987 | Leprevost |
| 4,705,502 A * | | 11/1987 | Patel .............................. 604/544 |
| 4,721,508 A * | | 1/1988 | Burton .......................... 604/338 |
| 4,784,133 A | | 11/1988 | Mackin |
| 4,836,204 A * | | 6/1989 | Landymore et al. .......... 606/215 |
| 4,976,692 A * | | 12/1990 | Atad ....................... 604/101.03 |
| 5,116,310 A | | 5/1992 | Seder et al. |
| 5,219,792 A | | 6/1993 | Kim et al. |
| 5,234,454 A | | 8/1993 | Bangs |
| 5,360,414 A | | 11/1994 | Yarger |
| 5,433,252 A | | 7/1995 | Wolf et al. |
| 5,527,280 A | | 6/1996 | Goelz |
| 5,545,220 A | | 8/1996 | Andrews et al. |
| 5,656,013 A * | | 8/1997 | Yoon ............................. 600/207 |
| 5,679,423 A | | 10/1997 | Shah |
| 5,782,800 A | | 7/1998 | Yoon |
| 5,807,333 A | | 9/1998 | Osborne et al. |
| 5,833,915 A | | 11/1998 | Shah |
| 5,879,499 A | | 3/1999 | Corvi |
| 5,924,456 A | | 7/1999 | Simon |
| 5,935,115 A | | 8/1999 | Espina |
| 5,951,514 A | | 9/1999 | Sahota |
| 5,996,639 A | | 12/1999 | Gans et al. |
| 6,022,313 A | | 2/2000 | Ginn et al. |
| 6,249,708 B1 | | 6/2001 | Nelson et al. |
| 6,270,477 B1 | | 8/2001 | Bagaoisan et al. |
| 6,291,543 B1 | | 9/2001 | Shah |
| 6,352,077 B1 | | 3/2002 | Shah |
| 6,460,541 B1 | | 10/2002 | Shah et al. |
| 6,478,789 B1 | | 11/2002 | Spehalski et al. |
| 6,663,646 B1 | | 12/2003 | Shah |
| 6,712,832 B2 | | 3/2004 | Shah |
| 6,805,662 B2 | | 10/2004 | Shah et al. |
| 6,827,710 B1 | | 12/2004 | Mooney et al. |
| 6,875,193 B1 | | 4/2005 | Bonnette et al. |
| 6,960,199 B2 | | 11/2005 | Burkett et al. |
| 7,112,186 B2 | | 9/2006 | Shah |
| 7,182,745 B2 | | 2/2007 | Desmond |
| 7,220,252 B2 | | 5/2007 | Shah |
| 7,470,251 B2 | | 12/2008 | Shah |
| 7,721,742 B2 | | 5/2010 | Kalloo et al. |
| 8,105,299 B2 * | | 1/2012 | Shah et al. ..................... 604/339 |
| 2003/0088209 A1 | | 5/2003 | Chiu et al. |
| 2005/0222329 A1 | | 10/2005 | Shah |
| 2006/0058576 A1 * | | 3/2006 | Davies et al. ................... 600/32 |
| 2006/0129094 A1 | | 6/2006 | Shah |
| 2006/0212064 A1 | | 9/2006 | Shah |
| 2007/0212559 A1 | | 9/2007 | Shah |
| 2007/0239110 A1 | | 10/2007 | Shah |
| 2007/0299463 A1 | | 12/2007 | Shah |
| 2008/0188802 A1 | | 8/2008 | Shah |
| 2008/0262449 A1 | | 10/2008 | Shah |
| 2008/0262450 A1 | | 10/2008 | Shah |
| 2009/0082724 A1 | | 3/2009 | Shah et al. |

FOREIGN PATENT DOCUMENTS

| | | |
|---|---|---|
| JP | 51-100833 A | 9/1976 |
| JP | 51-101084 A | 9/1976 |
| JP | 10-127771 A | 5/1998 |

* cited by examiner

OSTOMY BAG MOUNTING STRUCTURE

CROSS-REFERENCE TO RELATED APPLICATIONS

This application claims the benefit of priority under 35 U.S.C. §120 of U.S. Provisional Patent Application No. 60/913,529 filed Apr. 23, 2007 in the names of Tilak M. Shah, et al.

FIELD OF THE INVENTION

The present invention relates to a mounting structure that may be employed to fixture a port to the body of a subject for therapeutic or physiological intervention. In one embodiment, the invention relates to an ostomy bag mounting structure.

DESCRIPTION OF THE RELATED ART

In the treatment of a variety of disease states and physiological conditions, and in the course of medical intervention, it may be necessary to establish a portal at the surface of the human body to which can be joined a monitoring or treatment device, flow circuitry, etc.

One such circumstance involves the affixation to the body of an ostomy bag for removal of wastes of an individual. The ostomy bag requires a portal to which the bag can be secured to the individual. The portal includes an anchoring structure to which the ostomy bag can be coupled in waste-receiving relationship to the body of the wearer of the bag.

Prior portal structures have been unsatisfactory from the perspective of comfort of the individual accessorized with such structure, due to the sensitivity of the stoma. In addition, the portal structures of the prior art are frequently difficult to install on the body of the subject, so that they are properly anchored for subsequent use.

The present invention addresses such deficiencies.

SUMMARY OF THE INVENTION

The present invention relates to a mounting structure that may be employed to fixture a port to the body of a subject for therapeutic or physiological intervention.

The invention provides a mounting structure that is readily mountable on the body of a subject, in a safe, efficient and ready manner, and that in subsequent use is very comfortable to the wearer.

The invention in one aspect relates to a mounting structure for installation at a corporeal port opening, said mounting structure including a reentrant tube on an exterior surface of which is disposed at least one balloon, with a proximal everted portion of the tubing extending from the distal portion of the tubing, and with a gas flow passage associated with the tubing, for selective inflation of the balloon.

The invention in another aspect relates to a method of making a mounting structure for installation at a corporeal port, said method comprising vacuum thermoforming each of two sheets of thermoplastic material to form a balloon half-section on each of said two sheets, welding said two sheets to one another to form a tube communicating with a balloon constituted by said balloon half-sections, wherein the tube has distal and proximal portions extending from said balloon, and everting the tube to insert one of the distal and proximal portions through the other one of said portions so as to protrude therefrom, with the balloon circumscribing a reentrant portion of the inserted one of the distal and proximal portions, so that such portions are arranged as coaxial tube segments in relation to one another.

In such assembly of coaxial tube segments, the reentrant portion may be formed with circumferentially spaced apart, longitudinally extending ribs or lumens serving to reinforce the structure so that it does not collapse in use. The ribs or lumens are disposed between the coaxial tube segments in such manner, and may for example comprise from 2 to 16 ribs or lumens, as required for stiffening and reinforcement of the structure.

Other aspects, features and embodiments of the invention will be more fully apparent from the ensuing disclosure and appended claims.

DETAILED DESCRIPTION OF THE INVENTION, AND PREFERRED EMBODIMENTS THEREOF

The present invention relates to a mounting structure that may be employed to fixture a port to the body of a subject for therapeutic or physiological intervention. In one embodiment, the invention relates to an ostomy bag mounting structure.

Figure 1:
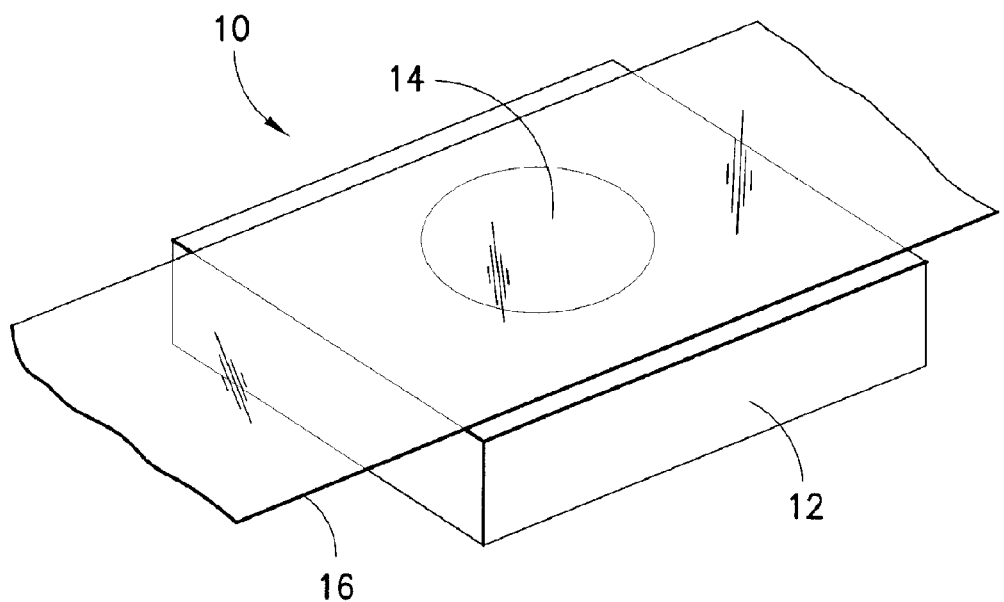
FIG. 1 is a schematic perspective view of a thin film material undergoing vacuum thermoforming, according to one embodiment of the present invention.

FIG. 1 is a schematic perspective view of a vacuum thermoforming system 10, and a thin polymeric film material sheet 16 undergoing vacuum thermoforming, according to one embodiment of the present invention. As shown, the polymeric film material sheet 16 is shown disposed on the top surface of the vacuum thermoforming block 12. The block features a vacuum thermoforming cavity 14 in the top surface, the cavity being coupled in vacuum-drawing relationship to an evacuation pump or other vacuum-applying device, whereby the portion of the film sheet 16 overlying the cavity 14 is drawn into the cavity by the resulting vacuum, and is shaped in conformity to the cavity. During the vacuum thermoforming operation, heat is applied to the block 12, e.g., by electrical resistance heating elements embedded therein, or in other suitable manner providing a temperature facilitating the vacuum thermoforming operation.

Figure 2:
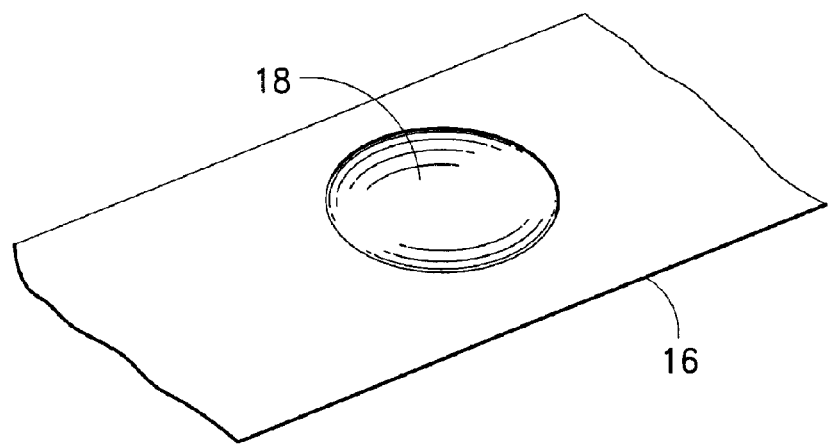
FIG. 2 is a perspective view of a vacuum thermoformed film, resulting from the thermoforming operation shown in FIG. 1.

FIG. 2 is a perspective view of a vacuum thermoformed film sheet 16, resulting from the thermoforming operation shown in FIG. 1. The sheet as illustrated contains a cavity 18 resulting from the vacuum thermoforming operation.

Figure 3:
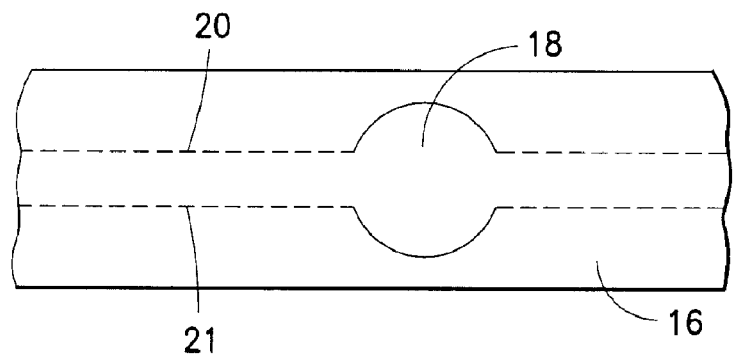
FIG. 3 is a top plan view of a vacuum thermoformed film showing the location of seam lines to be formed by welding of two vacuum thermoformed superposed sheets of thin film material.

FIG. 3 is a top plan view of the vacuum thermoformed film sheet 16 showing the cavity 18 therein as well as the location of seam lines 20 and 21 to be formed by welding of two vacuum thermoformed superposed sheets of thin film material.

Figure 4:
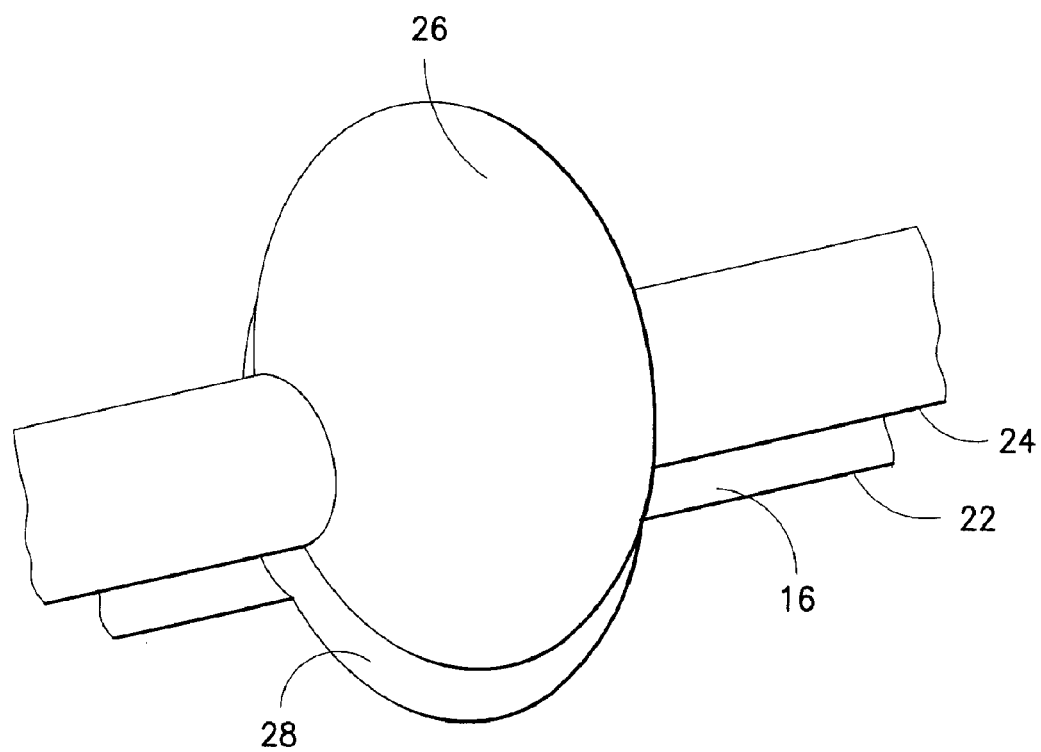
FIG. 4 is a perspective view of the superposed vacuum thermoformed sheets prior to bonding thereof.

FIG. 4 is a perspective view of the superposed vacuum thermoformed sheets 16 and 24 prior to bonding thereof. The bottom sheet 16 includes a balloon half-section formed by the cavity in the vacuum thermoforming block. The top sheet 24 includes a corresponding balloon half-section 26 formed by the vacuum thermoforming operation. The respective top and bottom sheets are brought in to register with one another, so that the edge of the top sheet mates with the edge 22 of the bottom sheet, to accommodate welding of the two sheets to one another at such edge. The two sheets may be of a thin-film character, viz., having a thickness of less than 10 mils.

It will be recognized that the welding of the two sheets to one another may be carried out with concurrent forming of the edge, or alternatively the respective sheets can be bonded to one another after the sheet has been cut or trimmed to a desired profile. The welding may be carried out by radiofrequency (RF) welding, by ultrasonic welding, by impulse heat sealing, or in any other suitable manner that is effective to form a continuous seam so that the welded article is leak-tight in use.

Figure 5:
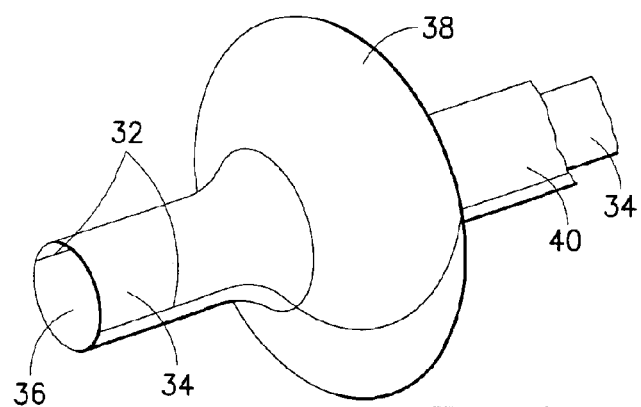
FIG. 5 is a perspective view of two superposed sheets of vacuum thermoformed polymeric material that have been welded to form seam lines.

FIG. 5 is a perspective view of two superposed sheets of vacuum thermoformed polymeric material that have been welded to form seam lines 32 extending longitudinally along the edges of the respective sheets. The welded sheets thereby form a support article, in which the tube 34 on the proximal side of the circumscribing balloon 38 is everted so that it is drawn through the tube 40 on the distal side of the circumscribing balloon. In this manner, an inlet/outlet opening 36 is provided in the support article.

Figure 5A:
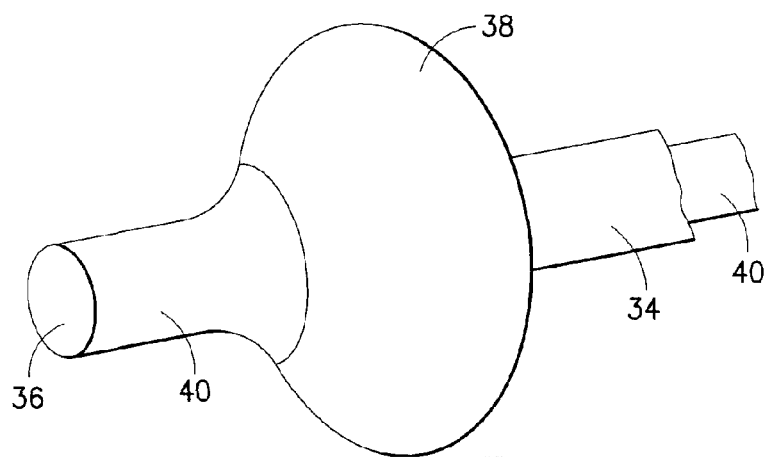
FIG. 5A is a perspective view of a support structure article according to another embodiment of the invention.

In the embodiment shown in FIG. 5, the seams 32 are on the outside of the mounting structure article. FIG. 5A is a corresponding view of a mounting structure article in which the entire article has been everted, followed by reentrantly inserting one of the tube segments into the other, to form the mounting structure article as shown, wherein the parts and components are correspondingly numbered to the same or similar parts and components in the FIG. 5 mounting structure article.

Figure 6:
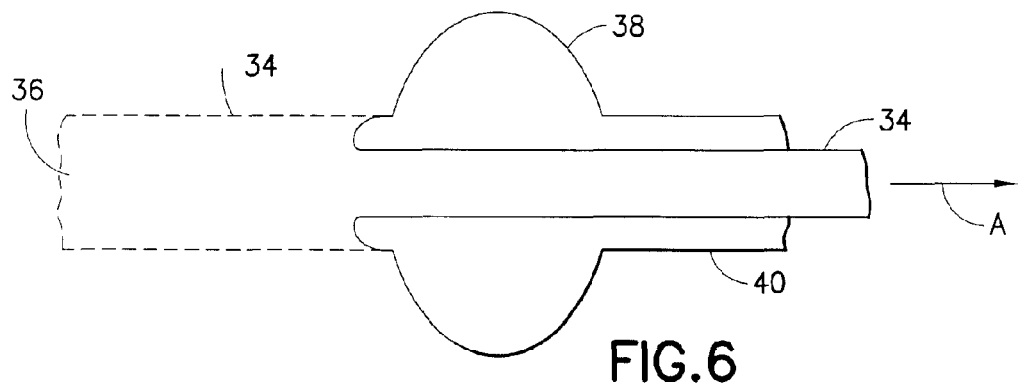
FIG. 6 is a schematic cross-sectional view of the article of FIG. 5, showing the eversion process.

FIG. 6 is a schematic cross-sectional view of the article of FIG. 5, showing the eversion process. The proximal portion 34 of the tube with open end 36 is everted (turned inside out), and the inverted tube then is drawn through the distal portion 40 in the direction indicated by arrow A, thereby forming a reentrant opening in proximity to the circumscribing balloon 38.

Figure 6A:
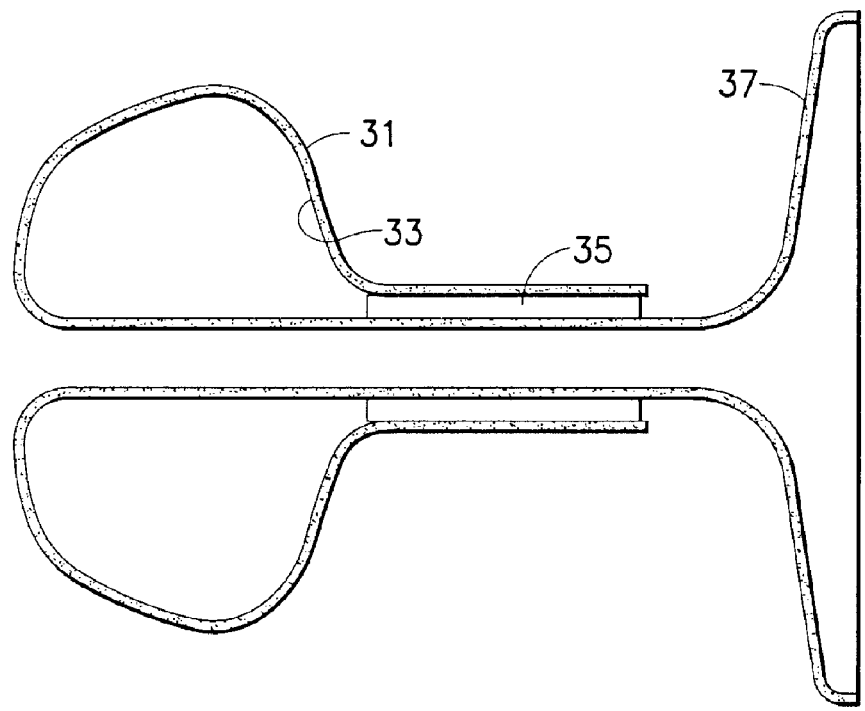
FIG. 6A is a schematic cross-sectional side elevation view of an everted balloon article according to another embodiment of the invention.

FIG. 6A is a schematic cross-sectional side elevation view of an everted balloon article according to another embodiment of the invention, wherein the balloon portion 31 and associated tube have been everted so that the welding seem 33 is on the inside of the balloon and reentrant tube portion, as illustrated. In this embodiment, a coaxial tube structure is formed by the reentrant tube segment, and one of the coaxial tube segments is formed with longitudinally extending rib elements 35 thereon, to stiffen the coaxial tube structure. In this embodiment, a second balloon element has been severed to form a flange 37, as hereinafter described in greater detail.

Figure 7:
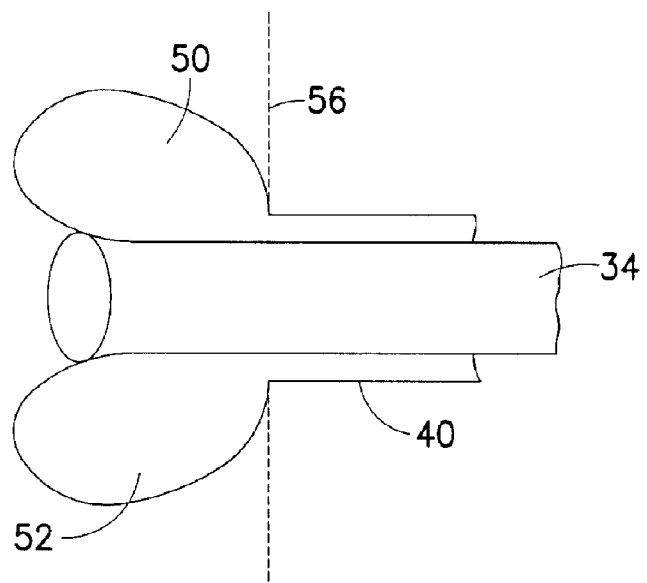
FIG. 7 is an elevation view of a mounting structure according to one embodiment of the invention, as positioned at the abdominal wall.

FIG. 7 is an elevation view of a mounting structure according to one embodiment of the invention, as positioned at the abdominal wall, schematically indicated by dashed line 56. The circumscribing balloon is shown in this view as including an upper portion 50 and a lower portion 52 between which the everted tube provides an opening which may engaged with an exterior device and coupled thereto, in communication with the interior cavity of the body bounded by the abdominal wall 56. For example, the opening, although shown schematically in FIG. 7 for ease of illustration, could be coupled with a fitting or joint structure that is engageable with a catheter, ostomy bag, infusion pump, or other therapeutic device.

The circumscribing balloon in the FIG. 7 mounting structure thus reposes against the exterior surface of the abdomen, and is inflated to provide a soft, deformable port assembly that accommodates the sensitivity of the stoma without adverse affect on comfort of the person to whom the mounting structure is affixed.

Figure 7A:
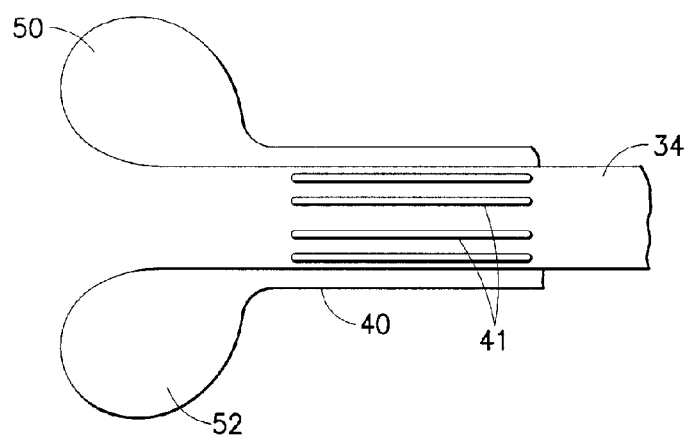

FIG. 7A is a cross sectional elevation side view of a mounting structure similar to that shown in FIG. 7, but having a series of welded ribs 41 to stiffen the coaxial tube segments. The ribs may be formed by welding, or may be discrete elements that are bonded to the tube wall surface in other manner, such as by adhesive welding, or other technique.

It will be appreciated that the circumscribing balloon formed by vacuum thermoforming and welding of the respective sheets of plastic film material can be rendered inflatable in any suitable manner. For example, a gas inflation tube may be placed between the superposed sheets that are welded to one another, so that the gas inflation tube is in communication with the balloon cavity, and exteriorly joinable to an inflation gas source. Alternatively, the sheets of thermoplastic film material may be longitudinally bonded along transversely spaced-apart lines, to form a gas inflation passage bounded by such bonded lines, so that when the welded mounting structure is everted, the gas inflation passage is interiorly disposed in gas flow communication with the balloon. It will therefore be apparent that a gas flow passage can be readily integrated in the mounting structure, so as to provide for inflation of the balloon, as desired.

Figure 8:
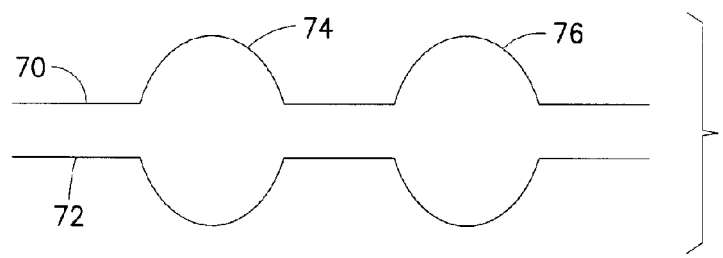
FIG. 8 is an exploded view of top and bottom vacuum thermoformed sheets, such as may be welded to one another, and everted to form a mounting structure with double balloon elements, according to yet another embodiment of the invention.

FIG. 8 is an exploded view of top and bottom vacuum thermoformed sheets 70 and 72, such as may be welded to one another, and everted to form a mounting structure with double balloon elements 74 and 76, according to yet another embodiment of the invention. For such purpose, the respective sheets of thermoplastic film material are placed over a vacuum thermoforming block with longitudinally spaced-apart vacuum cavities therein, to form the corresponding balloon half-sections. The resulting vacuum thermoformed film containing longitudinally spaced-apart balloon half-sections then may be welded to one another to form the mounting structure.

Figure 8A:
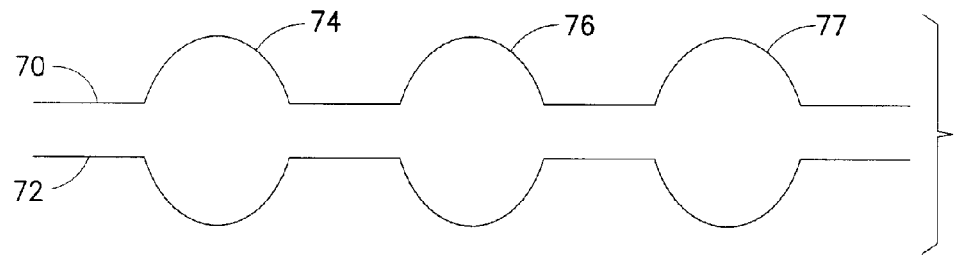
FIG. 8A is a view of a mounting structure including three balloons, as vacuum thermoformed in the respective sheets forming the mounting structure.

FIG. 8A is a corresponding view of a mounting structure including three balloons 74, 76 and 77, as vacuum thermoformed in the respective sheets 70 and 72 forming the mounting structure.

Figure 9:
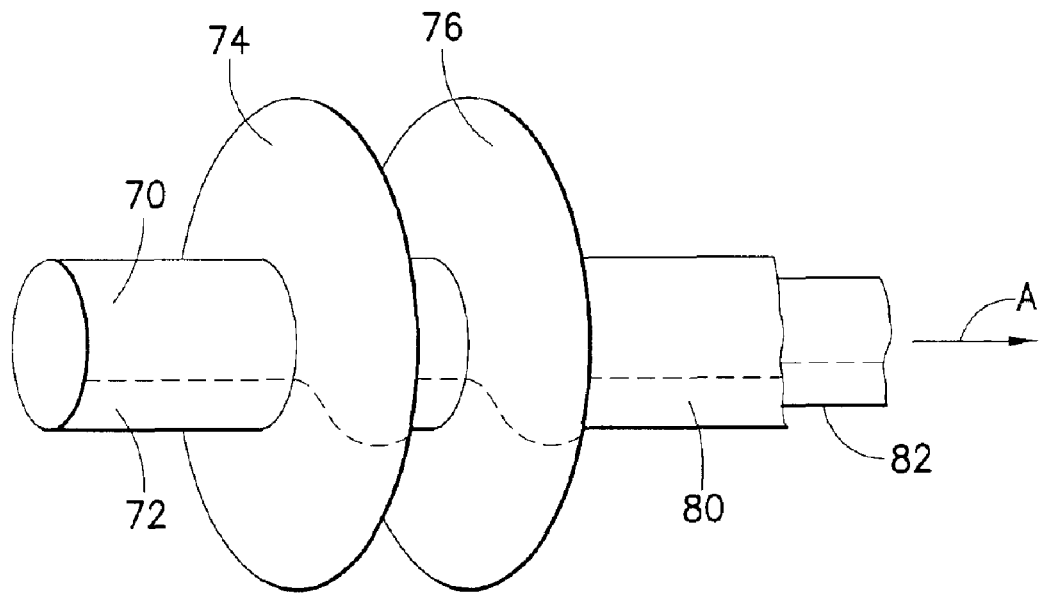
FIG. 9 is a perspective view of the mounting structure formed from the top and bottom vacuum thermoformed sheets shown in FIG. 8.

FIG. 9 is a perspective view of the mounting structure formed from the top and bottom vacuum thermoformed sheets 70 and 72 shown in FIG. 8. The proximal portion of the tube formed by the welded sheets is everted to form a reentrant end portion 82 that is drawn through the distal portion 80 of the tube, in the direction indicated by arrow A. The dashed line at the side of the mounting structure shows the weld seam line at which the respective top and bottom sheets 70 and 72 are bonded to one another. There is resultingly formed a double-balloon mounting structure, which may be installed so that one of the balloons is exterior to the body, proposed against the skin at the resulting portal opening, and so that the other of the balloons is interior to the body, reposed against the interior body surface at the portal opening.

Figure 9A:
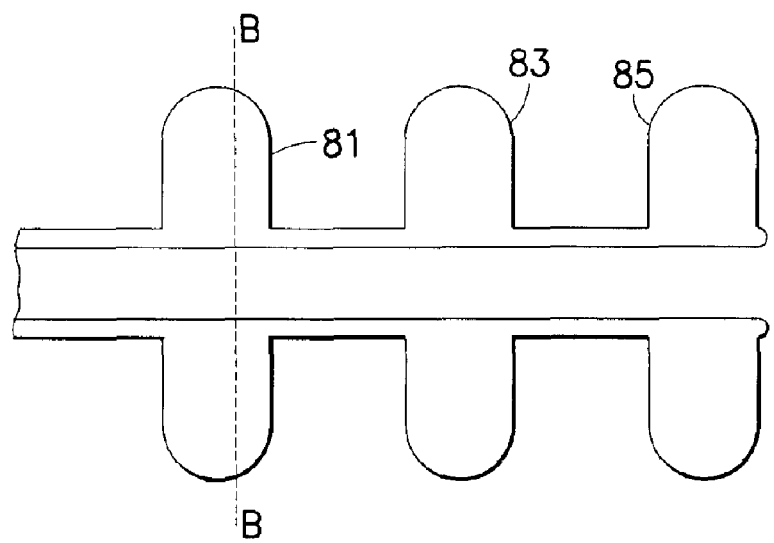
FIG. 9A is a schematic cross-section side elevation view of a mounting structure according to another embodiment of the invention, comprising an article including three vacuum thermoformed balloons.

FIG. 9A is a schematic cross-section side elevation view of a mounting structure according to another embodiment of the invention, comprising an article including three vacuum thermoformed balloons 81, 83 and 85. As shown, the tubing has been reentrantly inserted to form a coaxial tube structure. In this embodiment, the balloon 81 is shown with a dashed severing line B-B, which is severed to form a flange element, for coupling of the mounting structure with a connector or other coupled element or structure.

Figure 10:
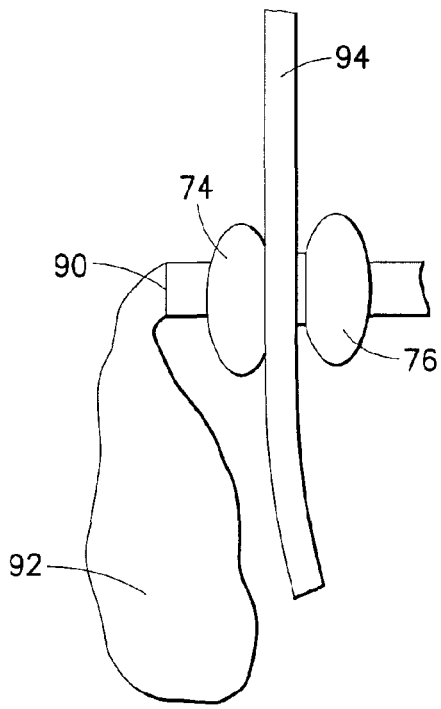
FIG. 10 is a side elevation view showing the mounting structure of FIG. 9 as mounted at the abdominal wall, with one balloon element interiorly disposed in the body, and with the other balloon element exteriorly disposed.

FIG. 10 is a side elevation view showing the mounting structure of FIG. 9 as mounted at the abdominal wall 94, with one balloon 76 interiorly disposed in the body, and with the other balloon 74 exteriorly disposed. The associated tube at its proximal end 90 is coupled with an ostomy bag 92 as illustrated. The respective interior and exterior balloons may be arranged with inflation gas feed lines communicating with one or both of such balloons, to selectively inflate same subsequent to installation on the body of the ostomy bag wearer. As discussed above, the gas inflation tube for each balloon may be formed by welded parallel lines that upon eversion of the tube form of gas flow passages that communicate with the interior volume of one or both balloons, to accommodate inflation thereof with an inflation medium, e.g., nitrogen or other inert gas, or alternatively a liquid inflation medium.

Figure 11:
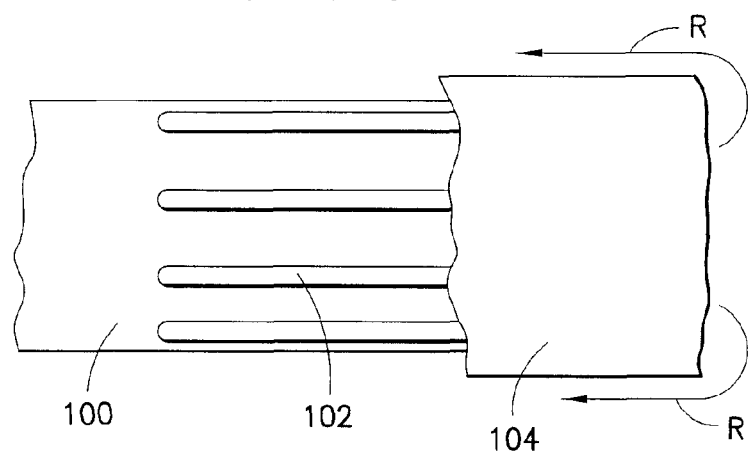
FIG. 11 is a schematic perspective view of an eversion operation in which a ribbed surface of a tube is being overlaid by an everted tube segment to dispose the rib elements between the resulting coaxial tube segments.

FIG. 11 is a schematic perspective view of an eversion operation in which a ribbed surface of a tube 100 is being overlaid by an everted tube segment 104 to dispose the rib elements 102 between the resulting coaxial tube segments.

Figure 12:
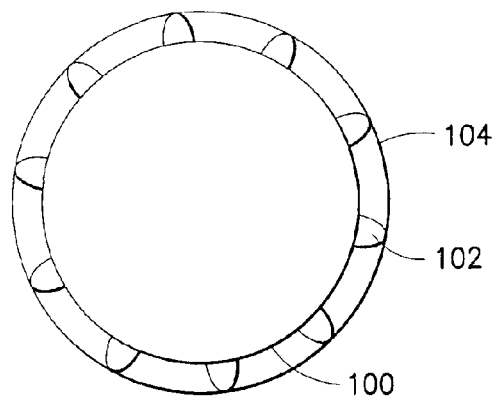
FIG. 12 is a cross-sectional view of the coaxial tube segments resulting from the eversion operation illustrated in FIG. 11.

FIG. 12 is a cross-sectional view of the coaxial tube segments 101 and 104 resulting from the eversion operation illustrated in FIG. 11, with the rib elements 102 disposed therebetween.

In lieu of the rib elements shown in FIGS. 11 and 12, lumen passages may be formed by longitudinally heat sealing folded-over sheets of a polymeric film parallel to the fold line, so that a lumen is formed and bounded by the fold line and the heat seal, or by simply superposing respective sheets and heat sealing same to one another along heat seal lines that are spaced-apart from one another, so that a passage is formed between successive heat seal lines. Alternatively, the coaxial tubing structure may be formed and subjected to longitudinal welding at space-apart intervals, to provide stiffening and reinforcement lumen passages. Such passages may be inflated with a suitable fluid, e.g., air or water, to impart improved sturdiness to the coaxial structure and enhanced comfort of the mounting structure when installed in a corporeal port. The lumen passages can be inflated or otherwise be of such dimensional character as to provide the requisite stiffening and reinforcement of the coaxial tube structure. Any number of rib or lumen elements may be employed for such purpose, e.g., 2-4, 6, 8, 12, or 16.

Figure 13:
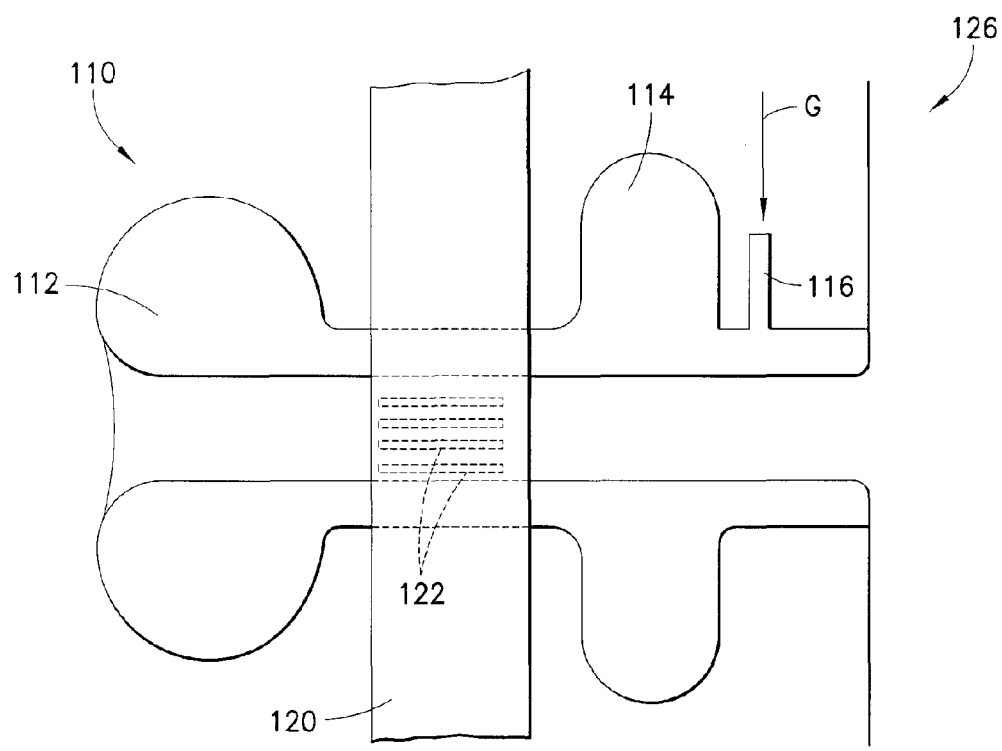
FIG. 13 is a schematic representation of a mounting structure according to one embodiment of the invention, as installed on the body of a wearer.

FIG. 13 is a schematic representation of a mounting structure 110 according to one embodiment of the invention, as installed on the body of a wearer. The mounting structure comprises an interior balloon 112 and exterior balloon 114, with longitudinal, spaced apart ribs 122 in the coaxial tubing annular space to provide increased stiffness and resistance to collapse. The intermediate coaxial tubing section is inserted through a port opening in the abdominal wall 120.

The mounting structure includes an inflation port 116, to which a source of inflation fluid, such as compressed air or water, maybe coupled to inflate the balloons, both interior and exterior, subsequent to initial installation of the mounting structure in the corporeal port. The mounting structure shown in FIG. 13 has been initially formed with a third balloon that has been severed to form the flange 126. The flange permits coupling with an external catheter, colostomy bag, or other apparatus, as appropriate to the therapeutic intervention associated with such mounting structure.

The polymeric film used in the mounting structure of the invention may be of any suitable type, and for example may comprise a thermoplastic elastomeric material, such as a polyurethane film material, or a laminate including barrier film, tie layers, and exterior layers.

The sheets of polymeric material may for example include polymeric materials such as polyethylene, polytetrafluoroethylene, polypropylene, polyurethane, polyvinylchloride, polyamide, polyether amide elastomer, styrenic elastomer, styrene isoprene butadiene (SIB)/styrene ethylene butadiene (SEB), and copolymers of monomers of the foregoing, etc., with polyurethane in general being preferred. The twin sheets of polymeric material used in forming the mounting structure of the invention may for example comprise a thermoplastic elastomer (TPE) material, and/or multilayer film, e.g., a laminate including barrier film, tie layers, and exterior layers. The two sheets that are welded to form the mounting structure of the invention may be the same as or different from one another.

The thickness of the sheets of polymeric material may be of any suitable dimensions, and may for example have a thickness in a range of from about one mil up to 50 mils.

The seam welding of the films may be carried out in any suitable manner, e.g., RF welding, impulse welding, ultrasonic welding, hotplate welding, hot wire welding, laser welding, etc. In general RF welding and laser welding are preferred techniques.

It will be appreciated that any number of interior passages can be provided in the tubing of the mounting structure of the invention, to accommodate flows of waste material from the body, or alternatively, introduction of fluid or materials into the body through the mounting structure. Accordingly, the tubing can be internally partitioned, such as by provision of welding lines to form multiple partition passages when the tubing is everted.

The invention therefore provides a mounting structure characterized by balloon elements that may be reposed against the surfaces on either side or at both sides of the port through which the tubing of the mounting structure is inserted. The mounting structure can be readily installed, with the balloon elements in a deflated state, with such balloon elements thereafter being inflated to provide a mounting structure at the port that is comfortable and avoids the deficiencies of prior port structures.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A mounting structure formed of a thermoplastic polymeric thin-film material for installation at a corporeal port opening, said mounting structure including a thermoplastic polymeric thin-film balloon and tube assembly comprising at least one balloon communicating with distal and proximal tube segments, said balloon and tube assembly including twin sheets of said thermoplastic polymeric thin-film material that are leak-tightly welded at edge seams to one another and include in each sheet at least one balloon half-section, wherein each balloon half-section communicates with distal and proximal tube segment half-sections, wherein said balloon and tube assembly comprises at least one balloon through which one of the distal and proximal tube segments communicating with the balloon extends, through an interior volume of the balloon and through the other of said distal and proximal tube segments, so that the balloon is internally supported only by the one of the distal and proximal tube segments extending through its interior volume in said assembly, and wherein ribs on said tube segments are oriented longitudinally thereon, said mounting structure further including a gas flow passage, for selective inflation of the balloon.

2. The mounting structure of claim 1, comprising a single balloon.

3. The mounting structure of claim 1, comprising two balloons, in spaced-apart relationship to one another.

4. The mounting structure of claim 1, wherein said thermoplastic polymeric thin-film material comprises a polymer selected from the group consisting of polyethylene, polytetrafluoroethylene, polypropylene, polyurethane, polyvinylchloride, polyamide, polyether amide elastomer, styrenic elastomer, styrene isoprene butadiene (SIB)/styrene ethylene butadiene (SEB), and copolymers of monomers of the foregoing.

5. The mounting structure of claim 1, wherein said thermoplastic polymeric thin-film material comprises a thermoplastic elastomer (TPE) material.

6. The mounting structure of claim 1, wherein said thermoplastic polymeric thin-film material comprises a laminate.

7. The mounting structure of claim 6, wherein said laminate comprises a barrier film, tie layer, and exterior layer.

8. The mounting structure of claim 1, wherein said tubing is coupled with an ostomy bag.

9. The mounting structure of claim 1, wherein said thermoplastic polymeric thin-film material has a thickness of less than 10 mils.

10. A method of making the mounting structure of claim 1 for installation at a corporeal port, said method comprising vacuum thermoforming each of two sheets of thermoplastic polymeric thin-film material to form a balloon half-section on each of said two sheets, welding said two sheets to one another to form a tube communicating with a balloon constituted by said balloon half-sections, wherein the tube has distal and proximal portions extending from said balloon, and everting the tube to insert one of the distal and proximal portions through the other one of said portions so as to protrude therefrom, with the balloon circumscribing a reentrant portion of the inserted one of the distal and proximal portions, so that such portions are arranged as coaxial tube segments in relation to one another.

11. The method of claim 10, wherein said welding comprises radiofrequency welding.

12. The method of claim 10, wherein said welding comprises ultrasonic welding.

13. The method of claim 10, wherein said welding comprises impulse heat sealing.

14. The method of claim 10, wherein said vacuum thermoforming is carried out to form two balloon half-sections on each of said two sheets.

15. The method of claim 14, wherein welding of the two sheets forms two balloons communicating with the tube, wherein the balloons are spaced apart from one another with an intermediate section of said tube therebetween.

16. The method of claim 10, wherein said two sheets are formed of a thermoplastic polymeric thin-film material.

17. The method of claim 16, wherein said thermoplastic polymeric thin-film material comprises a polymer selected from the group consisting of polyethylene, polytetrafluoroethylene, polypropylene, polyurethane, polyvinylchloride, polyamide, polyether amide elastomer, styrenic elastomer, styrene isoprene butadiene (SIB)/styrene ethylene butadiene (SEB), and copolymers of monomers of the foregoing.

18. The method of claim 16, wherein said thermoplastic polymeric thin-film material comprises a thermoplastic elastomer (TPE) material.

19. The method of claim 16, wherein said thermoplastic polymeric thin-film material comprises a laminate.

20. The method of claim 19, wherein said a laminate comprises a barrier film, tie layer, and exterior layer.

21. The method of claim 10, further comprising installing said mounting structure at a corporeal port.

22. The method of claim 21, further comprising coupling said tube with an ostomy bag.

23. The mounting structure of claim 1, wherein said one of the distal and proximal tube segments extending through the other of said distal and proximal tube segments includes on a facing surface thereof longitudinally oriented ribs or luminal passages therebetween.

24. The mounting structure of claim 1, including an integral flange comprising a partial balloon structure.

25. The mounting structure of claim 23, wherein said ribs or luminal passages are adapted to be inflated in use.

26. The mounting structure of claim 25, wherein said ribs or luminal passages are inflated with an inflation medium.

27. The mounting structure of claim 26, wherein said inflation medium comprises air or water.

28. The mounting structure of claim 1, comprising a single balloon, distal and proximal tube segments, and a flange.

29. The mounting structure of claim 1, comprising a double balloon, with overlapped distal and proximal tube segments therebetween.

30. The mounting structure of claim 29, wherein one of said overlapped distal and proximal tube segments on a facing surface thereof is reinforced by longitudinally oriented ribs or lumens.

31. The mounting structure of claim 29, further comprising a flange comprising a partial balloon structure.

* * * * *

UNITED STATES PATENT AND TRADEMARK OFFICE
CERTIFICATE OF CORRECTION

| | |
|---|---|
| PATENT NO. | : 8,167,859 B2 |
| APPLICATION NO. | : 12/106743 |
| DATED | : May 1, 2012 |
| INVENTOR(S) | : Tilak M. Shah |

It is certified that error appears in the above-identified patent and that said Letters Patent is hereby corrected as shown below:

Column 8, line 43: "...passages therebetween." should be -- ...passages. --.

Signed and Sealed this
Thirteenth Day of November, 2012

David J. Kappos
*Director of the United States Patent and Trademark Office*